United States Patent [19]

Tobiason

[11] Patent Number: 5,062,878

[45] Date of Patent: Nov. 5, 1991

[54] METHOD AND APPARATUS FOR CLEARING FLORA FROM SEWER LINES

[75] Inventor: Timothy W. Tobiason, Silver Creek, Nebr.

[73] Assignee: Toby's Chemical Company, Silver Creek, Nebr.

[21] Appl. No.: 436,071

[22] Filed: Nov. 13, 1989

[51] Int. Cl.$^5$ ...................... A01N 25/16; A01N 55/02
[52] U.S. Cl. ........................................... 71/65; 71/76; 71/79; 71/97; 71/DIG. 1
[58] Field of Search ................. 71/97, 65, DIG. 1, 76, 71/66, 67

[56] References Cited

U.S. PATENT DOCUMENTS

| | | | |
|---|---|---|---|
| 2,397,328 | 3/1946 | Ripley | 134/22 |
| 3,197,302 | 6/1965 | MacBride | 71/37 |
| 3,741,807 | 3/1971 | Horne | 71/65 |
| 4,425,154 | 1/1984 | Meyer et al. | 71/92 |

FOREIGN PATENT DOCUMENTS 4749685 12/1972 Japan ..................................... 71/56

OTHER PUBLICATIONS

Applicant's acknowledged prior art, Ser. No. 07/436,071, pp. 1, 2, and 7, instant specification.

Primary Examiner—Allen J. Robinson
Assistant Examiner—Brian M. Burn
Attorney, Agent, or Firm—Sean Patrick Suiter

[57] ABSTRACT

The present invention includes a herbicide having a phytocidal effect on roots and the like, and a foaming agent. The foaming agent consists of a gas releasing compound and a surfactant or detergent. To inhibit the growth of flora in or around sewer lines this mixture may be flushed into a sewer line. The gas releasing compound causes the surfactant or detergent to foam, and the foam acts as a carrier of the herbicide through the sewer line. Roots or the like growing within the sewer line are coated with the herbicide carrying foaming agent.

10 Claims, 1 Drawing Sheet

METHOD AND APPARATUS FOR CLEARING FLORA FROM SEWER LINES

BACKGROUND OF THE INVENTION

The present invention is directed generally to an improved method of carrying herbicides and more particularly to an apparatus and method of carrying herbicides to flora growing in or around sewer lines.

Sewer lines are prone to developing leaks. This is especially true of lines running from buildings adjacent to high traffic roadways, and in areas where earthquakes are common.

The openings that develop are often penetrated by roots. In time these roots can clog or rupture a sewer line. Once a clog or rupture occurs the sewer line must be removed and replaced. This replacement procedure is expensive and typically results in the loss of surrounding flora.

In order to prevent flora damage to sewer lines various herbicides have been used. The most common of these has been copper(II) sulfate. The prior art teaches flushing copper(II) sulfate down a toilet upstream from sewer lines where vegetation may potentially enter and damage a line.

The phytocidal effect of copper(II) sulfate is known to deter the growth of roots. However, the herbicidal application techniques known to the art are haphazard and expensive. For example, there is no practical method of determining how much, if any, of the herbicide has reached potentially damaging root growths. Herbicide applications are expensive, and over application may lead to the death of the flora.

Additionally, water is a poor carrying agent in sewer lines since it will not allow the entire line to be flushed with a herbicide, clearing only a free path along the normal fluid flow line.

In large industrial and/or urban sewer systems, it has been known to introduce a detergent and air from a hose connected to a high pressure air source so as to produce a herbicidal carrying agent. While such a procedure allows for the clearance of flora from areas above the normal flow line, this method is poorly suited for residential application. Where access to to the sewer line is through a toilet fixture, dragging air lines or a compressor into a home is inconvenient at best. More importantly, it is difficult if not impossible to cause foam generated in a toilet to be flushed down a sewer rather than overflow onto a bathroom floor.

Accordingly, a principal object of the present invention is to provide an improved method and apparatus for inhibiting the growth of flora in sewer lines.

Another object of the invention is to provide an economical method and apparatus for inhibiting the growth of flora in sewer lines.

Another object of the invention is to provide an easy to use method and apparatus for inhibiting the growth of flora in sewer lines.

Still another object of the invention is to provide a method and apparatus for inhibiting the growth of flora in sewer lines that will not unnecessarily damage the flora.

Still another object of the invention is to provide a method and apparatus for inhibiting the growth of flora in sewer lines that does not damage sewer lines.

Yet another object of the invention is to provide a method and apparatus for inhibiting the growth of flora in sewer lines that does not damage the environment.

Yet another object of the invention is to provide a method and apparatus for inhibiting the growth of flora in sewer lines that coats the entire cross-sectional area of the line.

SUMMARY OF THE INVENTION

The present invention includes a herbicide having a phytocidal effect on roots and the like, and a foaming agent. The foaming agent consists of a gas releasing compound and a surfactant or detergent.

A party wishing to inhibit the growth of flora in sewer lines may simply flush this mixture down a toilet of his home or business. The gas releasing compound causes the surfactant or detergent to foam, and the foam acts as a carrier of the herbicide throughout substantially the entire volume of the sewer line. The foam carries the herbicide above the level of a nonfoaming water and herbicide mixture flowing through the line. Additionally, the present invention allows foam to be introduced into a sewer line without the danger of spills, and without the need for dragging air generating equipment through a home.

Tree roots or the like growing within the sewer line are coated with the herbicide carrying foaming agent. This deters continued root growth in areas that may damage the sewer line without causing unnecessary damage to the tree or the like.

DESCRIPTION OF THE PREFERRED EMBODIMENT

Figure 1:
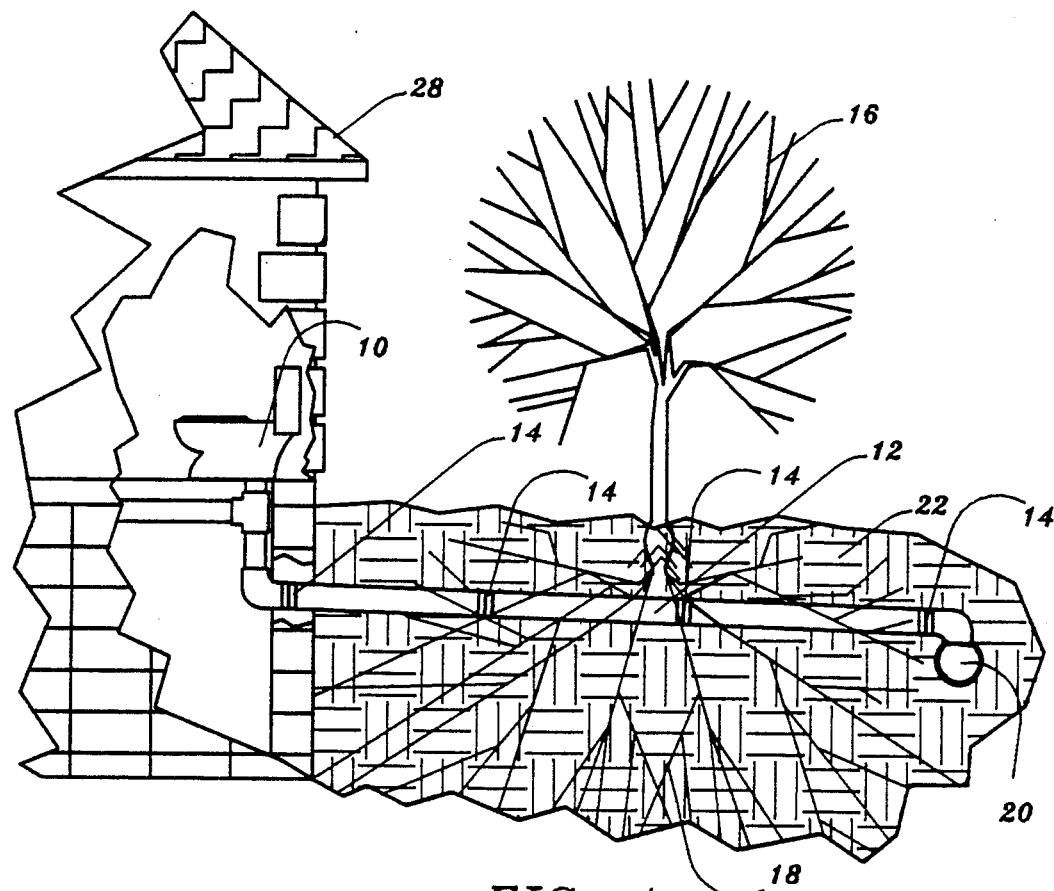
FIG. 1 is a partial sectional view of a sewer line system showing tree roots extending about the sewer line system.

The preferred embodiment of the invention utilizes copper(II) sulfate pentahydrate ($CuSO_4.H_2O$) as a herbicide, although many inorganic or organic herbicides would also work. The herbicide is carried by a foaming agent consisting of a gas releasing compound and a soap, syndet, or ABS (alkylbenzene sulfonate) detergent.

In order to generate a sufficient quantity of gas to cause the surfactant or detergent to foam sulfamic acid ($H_2NSO_3H$) and sodium bicarbonate ($NaHCO_3$) are used. The preferred embodiment utilizes a compound containing sodium sulfate, partially hydrolyzed starch, sodium dodecylbenzene sulfonate, oleoyl taurate, sodium bisulfate, PEG-3-lauramide, and dodecylbenzene sulfonic acid. This compound is distributed as "Mr. Bubble" by Airwick Industries, Inc. of Carlstadt, N.J. 07072.

Although the proportions of the mixture are not critical, and may be adjusted for the hardness of water, the compound of the preferred embodiment contains 907.2 grams (g) of copper(II) sulfate pentahydrate (3.75 mol); 136.0 g of sodium bicarbonate (1.62 mol); 90.7 g sulfamic acid (0.93 mol); and 9.0 g of "Mr. Bubble."

Another embodiment of the invention replaces the 9.0 g of "Mr. Bubble" with 9.0 g of dodecylbenzene sulfonic acid (0.03 mol).

Vibrations often cause the joints 14 in sewer lines 12 to be displaced and open. The roots 18 of trees 16 or the like seeking a Water source will grow into joint 14 openings. A party wishing to rid his sewer line of flora, such as tree or shrub roots, may simply empty the mixture into a toilet 10 within their home or business 28. The water and the mixture contained in the toilet 10 are then flushed into the sewer line 12. Any roots Within the sewer line 12 are coated by the foam-herbicide mixture 26 as it flows into a sewer trunk line 20.

Figure 2:
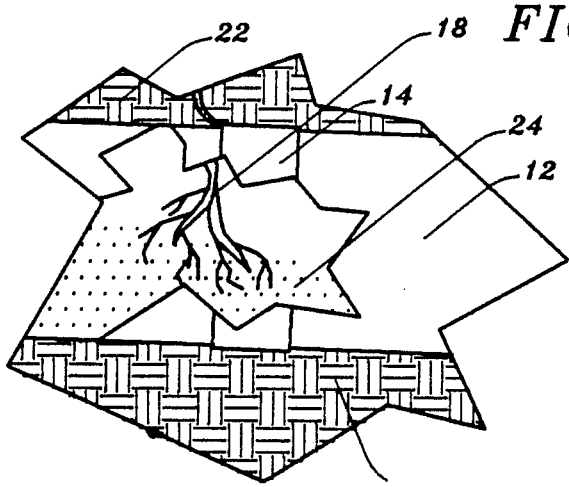
FIG. 2 is an enlarged partial sectional view showing water carrying herbicide through a sewer line.
Figure 3:
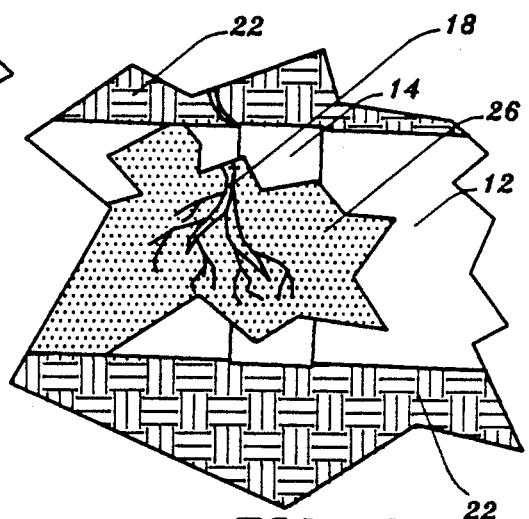
FIG. 3 is an enlarged partial sectional view showing how the foaming agent of the present invention allows herbicide to coat the entire cross-sectional area of the line.

FIG. 2 shows how simple flushing action provides an insufficient volume of water to coat the interior of the sewer line 12. Thus, roots 18 growing along the upper most interior surface of the sewer line 12 will be unaffected by a prior art treatment 24. FIG. 3 shows how the foaming agent 26 coats the entire interior area of the sewer line 12.

It is known in the art that copper naphthenate acts to chemically prune tap roots. Roots 18 will not penetrate soil 22 containing copper naphthenate. Another embodiment of the invention utilizes the foaming agent described before to carry copper naphthenate. After treatment the soil 18 surrounding openings within the sewer line 12 will be saturated by a chemical root pruning agent such as copper naphthenate, thus preventing roots from entering the sewer line 12

I claim:

1. A flora growth inhibitor product adapted for inhibiting the growth of flora in a sewer line, comprising:
   a herbicide;
   a dry acid;
   a carbonate; and
   a surfactant mixed with said carbonate and said acid whereby foam is produced in water for vertically elevating said herbicide such that flora roots growing within a sewer line are coated with said herbicide thereby inhibiting growth of flora in a sewer line.

2. The flora growth inhibitor product of claim 1, wherein said herbicide is a copper containing compound.

3. The flora growth inhibitor product of claim 1, wherein said carbonate is an alkali carbonate.

4. The flora growth inhibitor product of claim 1 wherein said carbonate is an alkali bicarbonate.

5. The flora growth inhibitor product of claim 1, wherein said dry acid is sulfamic acid.

6. A method of inhibiting the growth of flora in sewer lines, comprising:
   flushing a sewer line with a phytocidally effective quantity of the following compounds:
   a herbicide,
   a dry acid;
   a carbonate; and
   a surfactant mixed with gas releasing compound whereby foam is produced for vertically elevating said herbicide such that said herbicide coats the interior area of a sewer line.

7. The flora growth inhibitor method of claim 6, wherein said herbicide is a copper containing compound.

8. The flora growth inhibitor method of claim 6, wherein said carbonate is an alkali carbonate.

9. The flora growth inhibitor method of claim 6, wherein said carbonate is an alkali bicarbonate.

10. The flora growth inhibitor method of claim 6, wherein said dry acid is sulfamic acid.

* * * * *